(12) United States Patent
McAuley et al.

(10) Patent No.: US 9,333,315 B2
(45) Date of Patent: May 10, 2016

(54) BREATHING ASSISTANCE APPARATUS

(71) Applicant: Fisher & Paykel Healthcare Limited, Auckland (NZ)

(72) Inventors: Alastair Edwin McAuley, Dallas, TX (US); Craig Robert Prentice, Auckland (NZ); Oliver Gleeson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 14/846,226

(22) Filed: Sep. 4, 2015

(65) Prior Publication Data

US 2015/0374946 A1 Dec. 31, 2015

Related U.S. Application Data

(63) Continuation of application No. 14/333,134, filed on Jul. 16, 2014, which is a continuation of application No. 10/598,026, filed as application No. PCT/NZ2005/000023 on Feb. 18, 2005, now Pat. No. 8,783,257.

(30) Foreign Application Priority Data

Feb. 23, 2004 (NZ) ........................................ 531332
Aug. 6, 2004 (NZ) ........................................ 534606

(51) Int. Cl.
*A61M 16/06* (2006.01)
*A61M 16/16* (2006.01)
(Continued)

(52) U.S. Cl.
CPC ....... *A61M 16/0666* (2013.01); *A61M 16/0057* (2013.01); *A61M 16/0069* (2014.02);
(Continued)

(58) Field of Classification Search
CPC . A61M 15/08; A61M 16/06; A61M 16/0616; A61M 16/0633; A61M 16/0666; A61M 16/0683; A61M 16/0825; A61M 16/208; A61M 2210/0618; A61M 2240/00; A62B 18/00; A62B 18/02; A62B 18/08; A62B 18/084; A62B 35/00
See application file for complete search history.

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| CA | 131 16 62 | 12/1992 |
| CN | 217 253 8 | 7/1994 |

(Continued)

OTHER PUBLICATIONS

International Preliminary Report on Patentability (IPRP), International Application No. PCT/NZ2009/000219, mailed Apr. 12, 2011, 9 pages.

(Continued)

*Primary Examiner* — Annette Dixon
(74) *Attorney, Agent, or Firm* — Knobbe, Martens, Olson & Bear, LLP

(57) ABSTRACT

A nasal cannula can be shaped to fit within a user's nares, where the nasal cannula includes at least one prong allowing high flow delivery of humidified gases and creates positive airway pressure in the patient's airway. The prongs can have angled ends such that, in use, gases flowing through the prongs are directed to the user's nasal passages. The nasal cannula body can be partially swiveling and preferably has a ball joint connector. The nasal cannula can have at least one flared end prong that preferably seals within a patient's nare.

19 Claims, 10 Drawing Sheets

(51) Int. Cl.
*A61M 16/08* (2006.01)
*A61M 16/00* (2006.01)
*A61M 16/10* (2006.01)

(52) U.S. Cl.
CPC ....... *A61M16/0616* (2014.02); *A61M 16/0683* (2013.01); *A61M 16/08* (2013.01); *A61M 16/0816* (2013.01); *A61M 16/0825* (2014.02); *A61M 16/0875* (2013.01); *A61M 16/109* (2014.02); *A61M 16/16* (2013.01); *A61M 2205/0216* (2013.01)

(56) References Cited

U.S. PATENT DOCUMENTS

| | | | |
|---|---|---|---|
| 577,926 A | 3/1897 | Miller | |
| 718,470 A | 1/1903 | Jones | |
| 751,091 A | 2/1904 | Moran | |
| 770,013 A | 9/1904 | Linn | |
| 1,635,545 A | 7/1927 | Drager | |
| 2,296,150 A | 9/1942 | Dockson et al. | |
| 2,359,506 A | 10/1944 | Battley et al. | |
| 2,388,604 A | 11/1945 | Eisenbud | |
| 2,508,050 A | 5/1950 | Valente | |
| 2,693,800 A | 11/1954 | Caldwell | |
| 2,738,788 A | 3/1956 | Matheson et al. | |
| 2,843,121 A | 7/1958 | Hudson | |
| 2,859,748 A | 11/1958 | Hudson | |
| 3,490,452 A | 1/1970 | Greenfield | |
| 3,850,171 A | 11/1974 | Ball et al. | |
| 4,090,510 A | 5/1978 | Segersten | |
| D250,047 S | 10/1978 | Lewis et al. | |
| D250,131 S | 10/1978 | Lewis et al. | |
| D252,322 S | 7/1979 | Johnson | |
| 4,201,205 A | 5/1980 | Bartholomew | |
| 4,266,540 A | 5/1981 | Panzik et al. | |
| 4,354,488 A | 10/1982 | Bartos | |
| 4,367,735 A | 1/1983 | Dali | |
| 4,437,462 A * | 3/1984 | Piljay | A62B 18/084 128/207.11 |
| D293,613 S | 1/1988 | Wingler | |
| 4,753,233 A | 6/1988 | Grimes | |
| 4,782,832 A | 11/1988 | Trimble et al. | |
| 4,856,508 A | 8/1989 | Tayebi | |
| 4,915,105 A | 4/1990 | Lee | |
| 4,941,467 A | 7/1990 | Takata | |
| D310,431 S | 9/1990 | Bellm | |
| 4,971,051 A | 11/1990 | Toffolon | |
| 4,986,269 A | 1/1991 | Hakkinen | |
| 5,016,625 A | 5/1991 | Hsu et al. | |
| 5,042,478 A | 8/1991 | Kopala et al. | |
| D320,677 S | 10/1991 | Kumagai et al. | |
| D321,419 S | 11/1991 | Wallace | |
| 5,065,756 A | 11/1991 | Rapoport | |
| 5,094,236 A | 3/1992 | Tayebi | |
| 5,113,857 A | 5/1992 | Dickerman et al. | |
| 5,148,802 A | 9/1992 | Sanders et al. | |
| 5,231,979 A | 8/1993 | Rose et al. | |
| 5,245,995 A | 9/1993 | Sullivan et al. | |
| D340,317 S | 10/1993 | Cole | |
| 5,269,296 A | 12/1993 | Landis | |
| D354,128 S | 1/1995 | Rinehart | |
| D355,484 S | 2/1995 | Rinehart | |
| 5,477,852 A | 12/1995 | Landis et al. | |
| 5,533,506 A | 7/1996 | Wood | |
| 5,551,419 A | 9/1996 | Froehlich et al. | |
| 5,595,174 A | 1/1997 | Gwaltney | |
| 5,601,078 A | 2/1997 | Schaller et al. | |
| D378,610 S | 3/1997 | Reischel et al. | |
| 5,657,752 A | 8/1997 | Landis et al. | |
| 5,724,965 A | 3/1998 | Handke et al. | |
| 5,752,510 A | 5/1998 | Goldstein | |
| 5,884,624 A | 3/1999 | Barnett et al. | |
| 5,921,239 A | 7/1999 | McCall et al. | |
| 6,017,315 A | 1/2000 | Starr et al. | |
| 6,019,101 A | 2/2000 | Cotner et al. | |
| 6,050,260 A | 4/2000 | Daniell et al. | |
| 6,119,694 A | 9/2000 | Correa et al. | |
| 6,192,886 B1 | 2/2001 | Rudolph | |
| D440,302 S | 4/2001 | Wolfe | |
| 6,298,850 B1 | 10/2001 | Argraves | |
| 6,347,631 B1 | 2/2002 | Hansen et al. | |
| D455,891 S | 4/2002 | Biedrzycki | |
| 6,418,928 B1 | 7/2002 | Bordewick et al. | |
| 6,431,172 B1 | 8/2002 | Bordewick | |
| 6,435,181 B1 | 8/2002 | Jones, Jr. et al. | |
| 6,439,234 B1 | 8/2002 | Curti et al. | |
| 6,478,026 B1 | 11/2002 | Wood | |
| 6,491,034 B1 | 12/2002 | Gunaratnam et al. | |
| 6,561,188 B1 | 5/2003 | Ellis | |
| 6,561,191 B1 | 5/2003 | Kwok | |
| 6,581,594 B1 | 6/2003 | Drew et al. | |
| 6,581,601 B2 | 6/2003 | Ziaee | |
| 6,588,424 B2 | 7/2003 | Bardel | |
| 6,631,718 B1 | 10/2003 | Lovell | |
| 6,637,434 B2 | 10/2003 | Noble | |
| 6,644,315 B2 | 11/2003 | Ziaee | |
| 6,651,658 B1 | 11/2003 | Hill et al. | |
| 6,659,102 B1 | 12/2003 | Sico | |
| 6,662,803 B2 | 12/2003 | Gradon et al. | |
| 6,679,257 B1 | 1/2004 | Robertson et al. | |
| 6,679,265 B2 | 1/2004 | Strickland et al. | |
| 6,851,425 B2 | 2/2005 | Jaffre et al. | |
| 6,892,729 B2 | 5/2005 | Smith et al. | |
| 6,907,882 B2 | 6/2005 | Ging et al. | |
| 6,951,218 B2 | 10/2005 | Gradon et al. | |
| 7,004,165 B1 | 2/2006 | Salcido | |
| D520,140 S | 5/2006 | Chaggares | |
| D526,094 S | 8/2006 | Chen | |
| 7,096,864 B1 | 8/2006 | Mayer et al. | |
| 7,201,169 B2 * | 4/2007 | Wilkie | A61M 16/06 128/207.13 |
| 7,207,333 B2 | 4/2007 | Tohara | |
| 7,210,481 B1 | 5/2007 | Lovell et | |
| 7,219,669 B1 | 5/2007 | Lovell et al. | |
| 7,318,437 B2 | 1/2008 | Gunaratnam et al. | |
| 7,353,827 B2 | 4/2008 | Geist | |
| 7,896,003 B2 | 3/2011 | Matula et al. | |
| 8,042,539 B2 | 10/2011 | Chandran et al. | |
| 8,443,807 B2 | 5/2013 | McAuley et al. | |
| D686,313 S | 7/2013 | Matula et al. | |
| 8,479,741 B2 | 7/2013 | McAuley et al. | |
| 8,783,257 B2 | 7/2014 | McAuley et al. | |
| 2002/0046755 A1 | 4/2002 | Voss | |
| 2002/0053347 A1 | 5/2002 | Ziaee | |
| 2002/0059935 A1 | 5/2002 | Wood | |
| 2002/0096178 A1 | 7/2002 | Ziaee | |
| 2003/0005933 A1 | 1/2003 | Izuchukwu | |
| 2003/0079749 A1 | 5/2003 | Strickland et al. | |
| 2003/0164170 A1 | 9/2003 | Drew et al. | |
| 2003/0172936 A1 | 9/2003 | Wilkie et al. | |
| 2003/0196656 A1 | 10/2003 | Moore | |
| 2003/0196659 A1 | 10/2003 | Gradon et al. | |
| 2003/0196664 A1 | 10/2003 | Jacobson | |
| 2003/0200970 A1 * | 10/2003 | Stenzler | A61M 16/0666 128/207.18 |
| 2004/0067333 A1 | 4/2004 | Amarasinghe | |
| 2004/0211427 A1 | 10/2004 | Jones et al. | |
| 2004/0226566 A1 | 11/2004 | Gunaratnam et al. | |
| 2005/0011524 A1 * | 1/2005 | Thomlinson | A61M 16/0666 128/207.18 |
| 2005/0028822 A1 | 2/2005 | Sleeper et al. | |
| 2005/0076913 A1 | 4/2005 | Ho et al. | |
| 2005/0150497 A1 | 7/2005 | Eifler et al. | |
| 2005/0205096 A1 | 9/2005 | Matula et al. | |
| 2005/0235999 A1 | 10/2005 | Wood et al. | |
| 2006/0060200 A1 | 3/2006 | Ho et al. | |
| 2006/0107958 A1 | 5/2006 | Sleeper | |
| 2006/0124131 A1 * | 6/2006 | Chandran | A61M 16/06 128/206.28 |
| 2006/0137690 A1 | 6/2006 | Gunaratnam et al. | |
| 2006/0174887 A1 | 8/2006 | Chandran et al. | |
| 2006/0196511 A1 | 9/2006 | Lau et al. | |
| 2006/0237018 A1 | 10/2006 | McAuley et al. | |

(56) References Cited

U.S. PATENT DOCUMENTS

| | | |
|---|---|---|
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0163600 A1 | 7/2007 | Hoffman |
| 2007/0295335 A1 | 12/2007 | Nashed |
| 2008/0041388 A1 | 2/2008 | McAuley et al. |
| 2008/0047560 A1 | 2/2008 | Veliss et al. |
| 2008/0060648 A1 | 3/2008 | Thornton et al. |
| 2008/0060657 A1 | 3/2008 | McAuley et al. |
| 2008/0099024 A1 | 5/2008 | Gunaratnam et al. |
| 2008/0196728 A1 | 8/2008 | Ho |
| 2008/0264422 A1 | 10/2008 | Fishman |
| 2009/0044808 A1 | 2/2009 | Guney et al. |
| 2009/0120442 A1 | 5/2009 | Ho |
| 2010/0307502 A1 | 12/2010 | Rummery et al. |
| 2010/0313891 A1 | 12/2010 | Veliss et al. |
| 2011/0308520 A1 | 12/2011 | McAuley et al. |
| 2012/0125339 A1 | 5/2012 | Ho et al. |
| 2012/0132209 A1 | 5/2012 | Rummery et al. |
| 2015/0013678 A1 | 1/2015 | McAuley |
| 2015/0297855 A1 | 10/2015 | McAuley et al. |
| 2016/0038705 A1 | 2/2016 | McAuley et al. |
| 2016/0038706 A1 | 2/2016 | McAuley et al. |
| 2016/0038707 A1 | 2/2016 | Allan et al. |

FOREIGN PATENT DOCUMENTS

| | | |
|---|---|---|
| CN | 1784250 | 6/2006 |
| CN | 1901961 A | 1/2007 |
| CN | 1988930 A | 6/2007 |
| CN | 101214402 | 7/2008 |
| CN | 101541380 | 9/2009 |
| EP | 0747078 | 12/1996 |
| EP | 2 130 563 A1 | 12/2009 |
| EP | 1646910 | 8/2015 |
| FR | 2658725 | 8/1991 |
| FR | 2749176 | 12/1997 |
| GB | 190 224 431 | 12/1902 |
| GB | 880 824 | 10/1961 |
| GB | 1 467 828 | 3/1977 |
| JP | H09-010311 | 1/1997 |
| JP | 2005-529687 | 10/2005 |
| JP | 2007-516750 | 6/2007 |
| JP | 2007-527271 | 9/2007 |
| WO | WO98/18514 | 5/1998 |
| WO | WO 99/04842 A1 | 2/1999 |
| WO | WO99/58181 | 11/1999 |
| WO | WO 00/69497 | 11/2000 |
| WO | WO 00/74758 | 12/2000 |
| WO | WO01/41854 | 6/2001 |
| WO | WO 01/97892 A1 | 12/2001 |
| WO | WO02/074372 | 9/2002 |
| WO | WO 2004/041341 | 5/2004 |
| WO | WO 2004/073778 | 9/2004 |
| WO | WO 2005/021075 | 3/2005 |
| WO | WO 2005/051468 | 6/2005 |
| WO | WO 2005/086946 | 9/2005 |
| WO | WO 2007/022562 A1 | 3/2007 |
| WO | WO 2007/041786 | 4/2007 |
| WO | WO 2007/147088 A2 | 12/2007 |
| WO | WO 2008/007985 A1 | 1/2008 |
| WO | WO 2008/070929 A1 | 6/2008 |
| WO | WO 2008/106716 A1 | 9/2008 |
| WO | WO2008/148086 | 12/2008 |
| WO | WO 2009/052560 A1 | 4/2009 |
| WO | WO 2009/059353 A1 | 5/2009 |
| WO | WO 2009/092057 A1 | 7/2009 |
| WO | WO 2009/139647 A1 | 11/2009 |

OTHER PUBLICATIONS

International Search Report, International Application No. PCT/NZ2009/000219, mailed Feb. 2, 2010, 3 pages.
English Translation of Chinese Examination Report; Application No. 2007800266164; 5 pages.
English Translation of First Office Action for Chinese Application No. 201210080441.8 dated Mar. 24, 2014, in 4 pages.
Examination Report; Australian Application No. 2007273324; dated May 22, 2012; 3 pages.
International Search Report for International Application No. PCT/NZ2007/000185, dated Oct. 31, 2007, in 3 pages.
Second Chinese Office Action for Chinese Patent Application No. 201210080441.8 dated Dec. 1, 2014 in 11 pages (with English translation).
Australian Examination Report for Patent Application No. 2012265597 dated Dec. 19, 2013, in 5 pages.
Canadian Examination Report for Application No. 2655839 dated Oct. 4, 2013, in 2 pages.
English Translation of Chinese Examination Report; Chinese Application No. 2007800266164; 5 pages.
International Search Report; PCT/NZ2009/000072; dated Jul. 28, 2009; 3 pages.
UK Search and Examination Report; Mar. 14, 2013; Application No. GB1210075.6; 2 pages.
UK Examination Report; dated May 9, 2013; Application No. GB1119385.1; 4 pages.
Australian Examination Report; dated Mar. 4, 2014; Application No. 2010246985; 5 pages.
English Translation of JP Examination Report; dated Feb. 10, 2014; Application No. 2012-510418; 4 pages.
Chinese Examination Report; dated Mar. 27, 2014; Chinese Application No. 201080028029.0; 16 pages.
GB Combined Search and Examination Report; dated May 7, 2014; Application No. GB1406402.6; 6 pages.
GB Combined Search and Examination Report; dated May 7, 2014; Application No. GB1406401.8; 4 pages.
JP Examination Report, Application No. 2012-538784; 3 pages.
Australian Examination Report; dated Aug. 14, 2015; Application No. 2015202814; 8 pages.
Chinese Examination Report; dated Jul. 17, 2015; Application No. 201080061122.1; 10 pages.
Chinese Examination Report; dated Sep. 14, 2015; Application No. 201080028029.0; 3 pages.
European Extended Search Report; dated Sep. 4, 2015; Application No. 10830251.4; 7 pages.
European Extended Search Report; dated Sep. 8, 2015; Application No. 10774623.2; 7 pages.
Japanese Examination Report; dated Jul. 22, 2015; Application No. 2015-098324; 8 pages.
Japanese Examination Report; dated Aug. 5, 2015; Application No. 2012-538784; 8 pages.
Australian Examination Report; dated Jan. 9, 2015; Application No. 2010241390; 4 pages.
English Translation of Chinese Examination Report; dated Sep. 3, 2014; Application No. 201080061122.1; 9 pages.
Second Chinese Office Action; dated Jan. 19, 2015; Application No. 201080028029.0; 16 pages.
EPO Search Report; dated Apr. 2, 2014; Application No. 09819444.2; 8 pages.

* cited by examiner

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTIONS

1. Field of the Inventions

The present inventions relate to apparatuses for treating sleep apnoea. For example, the present inventions can provide a nasal positive airway pressure device.

2. Description of the Related Art

Obstructive Sleep Apnoea (OSA) is a sleep disorder that affects up to at least 5% of the population in which muscles that normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a nasal mask. The pressurised air supplied to the patient effectively assists the muscles to keep the patient's airway open, eliminating the typical OSA sleep pattern.

The procedure for administering CPAP treatment has been well documented in both the technical and patent literature. Briefly stated, CPAP treatment acts as a pneumatic splint of the airway by the provision of a positive pressure, usually in the range 4 to 20 cm $H_2O$. The air is supplied to the airway by a motor driven blower whose outlet passes via an air delivery hose to a nose (or nose and/or mouth) mask sealingly engaged to a patient's face by means of a harness or other headgear. An exhaust port is provided in the delivery tube proximate to the mask. More sophisticated forms of positive airway pressure devices, such as bi-level devices and auto-titrating devices, are described in U.S. Pat. No. 5,148, 802 of Respironics, Inc. and U.S. Pat. No. 5,245,995 of Rescare Limited, respectively.

U.S. Pat. No. 5,477,852 of Airways Ltd, Inc. discloses a nasal positive airway pressure device that has a pair of nasal members each having a cannula tip to be inserted into the nares of the patient. Each cannula is tapered from a substantially circular cross-section outside the patient's nostril to a substantially oval cross-section at the tip inserted into the nostril. An inflatable cuff surrounds each cannula with the interior space of the cuff communicating with the lumen of the cannula through at least one aperture in the sidewall of the cannula. The nasal members are connected to one or more flexible hoses that, in turn, are connected to a source of positive air pressure. In use, positive air pressure is supplied to each cannula tip through the air hoses and nasal members. The positive air pressure inflates the cuffs to hold the nasal members in place and to effect treatment. The nasal device of U.S. Pat. No. 5,477,852 is attached to headgear that is located about a patient's head; this headgear could be considered by many patients as cumbersome and uncomfortable.

Conventional nasal masks used for administrating CPAP treatment are also considered uncomfortable and cumbersome, and prior art nasal masks and the like are noisy (due to air leaks). These disadvantages in many cases are a formidable obstacle to patient acceptance of such treatment. Therefore, a substantial number of patients either cannot tolerate treatment or choose to forego treatment. It is believed a substantial number of such patients could benefit from a nasal positive airway pressure apparatus that is more convenient to use and comfortable to wear, thereby resulting in increased treatment compliance.

As oxygen is supplied as a dry gas it is well known in the art to either heat and/or humidify gases before delivering them for breathing by a patient. In particular when delivering oxygen, or oxygen or air mixture, it has proven beneficial to humidify the gases first. In WO01/41854 of Vapotherm, Inc. a system is disclosed that allows the delivery of humidified oxygen through a nasal cannula. This system uses a narrow bore conduit and nasal cannula with a high resistance to gas flows, thereby requiring the oxygen be of a high pressure. Air, as well as oxygen can also be passed down the conduit and nasal cannula and it too must be of a high pressure. This system allows the delivery of high flows of oxygen enriched air to the patient, but is limited in the flows achievable due to the narrow bore of the cannula resulting in high resistance gas flow and excessive velocity and noise upon exiting the cannula. Furthermore, the narrowness of the nasal cannula in this system allows easy expiration of gases between the prongs and nares and therefore does not create any positive airway pressure.

Innomed Technologies, Inc. manufactures a nasal cannula device called the NASALAIRE™. In this device air or oxygen travels down a wide bore conduit to nasal cannula. The NASALAIRE™ creates a physical seal between the nares and itself, and relies on the absence of leaks around itself and the nares to deliver pressure supplied by a continuous positive airway pressure (CPAP) blower to the airway of the wearer.

SUMMARY OF THE INVENTIONS

It is an object of at least some of the present inventions to provide a breathing assistance apparatus which goes someway to overcoming the above mentioned disadvantages or which will at least provide the public a useful choice.

Accordingly in a first aspect the present inventions consists in a breathing assistance apparatus comprising:

nasal cannula, shaped to fit within a user's nares, and adapted to deliver said humidified gases to said user, a pressurised source of gases, transportation means adapted to, in use, be in fluid communication with said source of gases and said nasal cannula and adapted to in use convey said gases to said user, wherein said nasal cannula including at least one prong allowing high flow delivery of said humidified gases and creating a positive airway pressure in said patient's airway, said at least one prong having an angled end, such that in use, gases flowing through said prong are directed to said user's nasal passages.

In a second aspect the present inventions consists in a breathing assistance apparatus comprising:

nasal cannula, shaped to fit within a user's nares, a pressurised source of gases, transportation means adapted to, in use, be in fluid communication with said source of gases and said nasal cannula and adapted to in use convey said gases to said user, wherein said nasal cannula are adapted to deliver said humidified gases to said user, said nasal cannula including at least one prong allowing high flow delivery of said humidified gases and creating positive airway pressure in said patient's airway, said at least one prong having an end that is flared outwardly.

To those skilled in the art to which the inventions relate, many changes in construction and widely differing embodiments and applications of the invention will suggest themselves without departing from the scope of the inventions as defined in the appended claims. The disclosures and the descriptions herein are purely illustrative and are not intended to be in any sense limiting.

BRIEF DESCRIPTION OF THE DRAWINGS

Preferred forms of the present inventions will now be described with reference to the accompanying drawings.

DETAILED DESCRIPTION OF THE PREFERRED EMBODIMENT

Whether used in a hospital environment or in a home environment, the nasal cannula of the present inventions will generally have associated three main pieces of apparatus. Firstly, an active humidifier, which that controls the temperature of a heater plate heating a body of water to achieve a desired temperature and humidity of the gases being humidified. Secondly, a transport conduit from the humidifier to the patient is also required, which is preferably heated to reduce condensation, or "rain out". Thirdly, a cannula designed to fit into the nasal cavity and deliver humidified, pressurized gases. In particular, in one embodiment the nasal cannula of the present invention has two flared end prongs that seal within a patient's nares, although in some embodiments the cannula may have a single prong. The cannula prongs are shaped such that a step is created between them so that the prongs abut the user's nasal septum in use. Furthermore, the gripping action of the sides of the prongs to the user's septum in use prevents the prongs from dislodging from the user's nares. In another embodiment the prongs of the nasal cannula are angled toward one another as well as having an angled profile at the outlet of gases, such that gases flow from the prongs flows back into the nasal passage and is not forced up into the rest of the nasal cavity.

Figure 1:
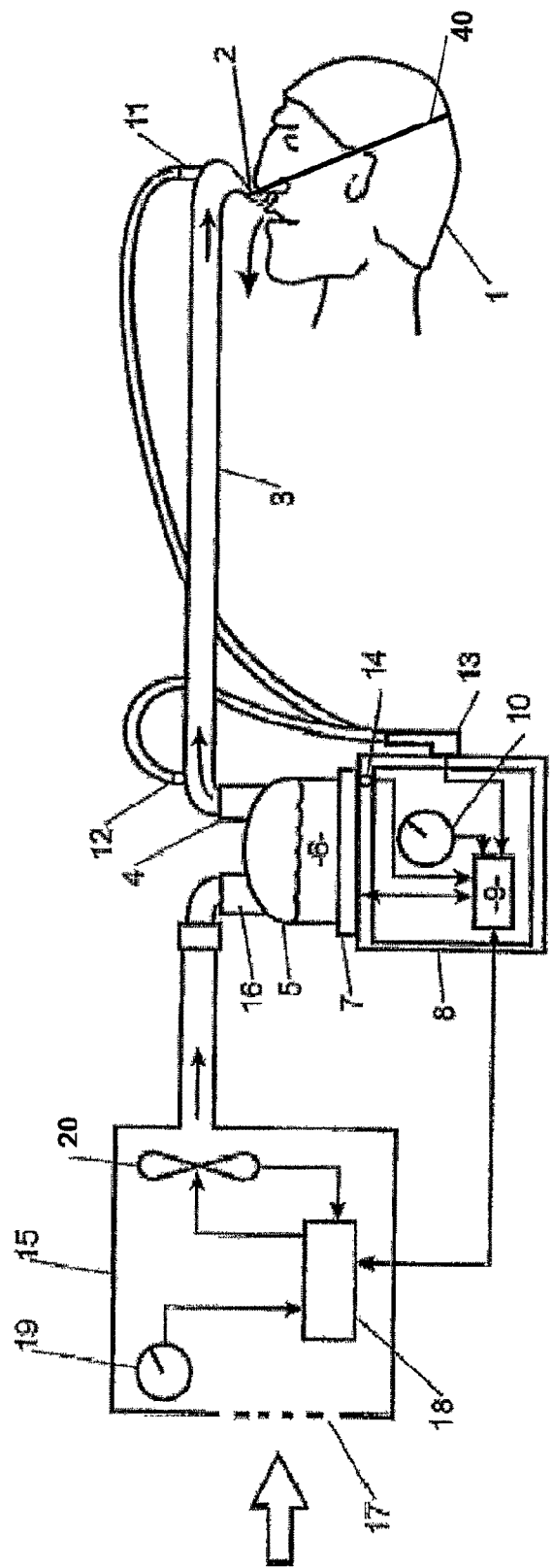
FIG. 1 is a block diagram of a system providing humidified continuous positive airway pressure to a user as might be used in conjunction with a nasal cannula of the present invention.

With reference to FIG. 1 a humidified Continuous Positive Airway Pressure (CPAP) system is shown in which a patient 1 is receiving humidified and pressurised gases through the nasal cannula 2 of the present invention. The cannula 2 is connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 that contains a volume of water 6. The inspiratory conduit 3 may contain heating means or heater wires (not shown) which heat the walls of the conduit to reduce condensation of humidified gases within the conduit. The humidification chamber 6 is preferably formed from a plastics material and may have a highly heat conductive base (for example an aluminium base) which is in direct contact with a heater plate 7 of humidifier 8. The humidifier 8 is provided with control means or electronic controller 9 that may comprise a microprocessor based controller executing computer software commands stored in associated memory.

The controller 9 receives input from sources such as user input means or dial 10 through which a user of the device may, for example, set a predetermined required value (preset value) of humidity or temperature of the gases supplied to patient 1. The controller may also receive input from other sources; for example, temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. A flow of gases (for example air) is provided to the chamber through inlet 16 from a gases supply means or blower 15. As the volume of water 6 within humidification chamber 5 is heated, water vapour begins to fill the volume of the chamber above the water's surface and is passed out of the humidification chamber 5 through outlet 4. Exhaled gases from the patient's mouth are passed directly to ambient surroundings in FIG. 1.

The blower 15 is provided with variable pressure regulating means or a variable speed fan 20 which draws air or other gases through the blower inlet 17. The speed of the variable speed fan 20 is controlled by the electronic controller 18 (or alternatively the function of the controller 18 could carried out by the controller 9) in response to inputs from the controller 9 and a user set predetermined required value (preset value) of pressure or fan speed via the dial 19.

Flared Prong Nasal Cannula

Figure 2:
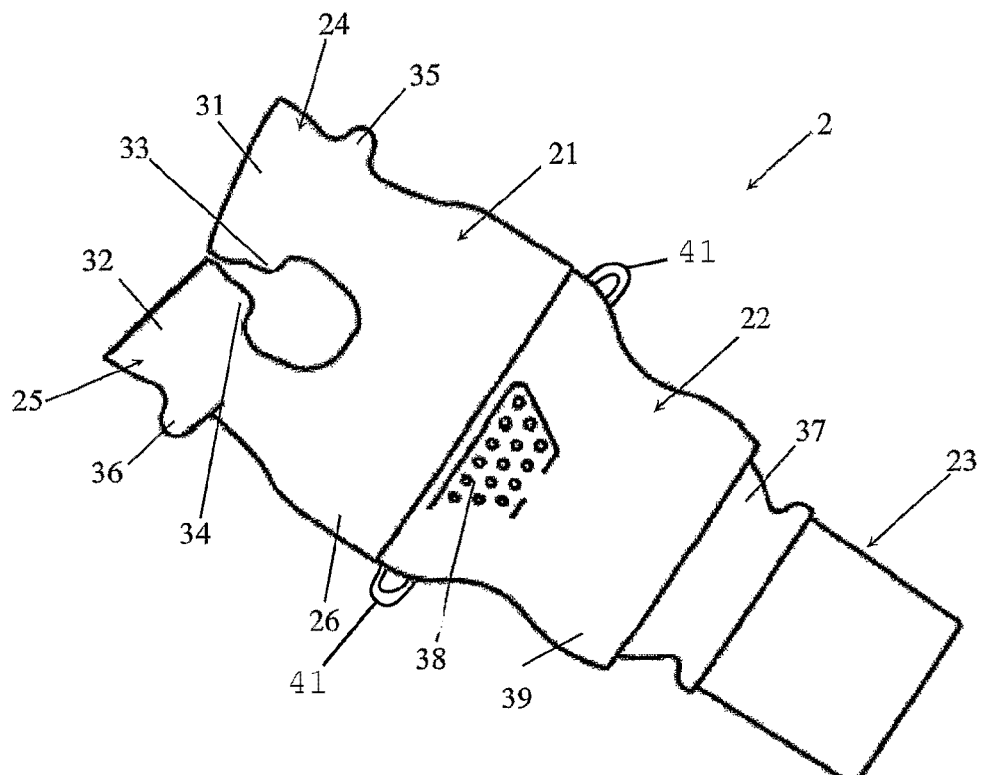
FIG. 2 is a perspective view of a first embodiment of the nasal cannula of the present invention.
Figure 3:
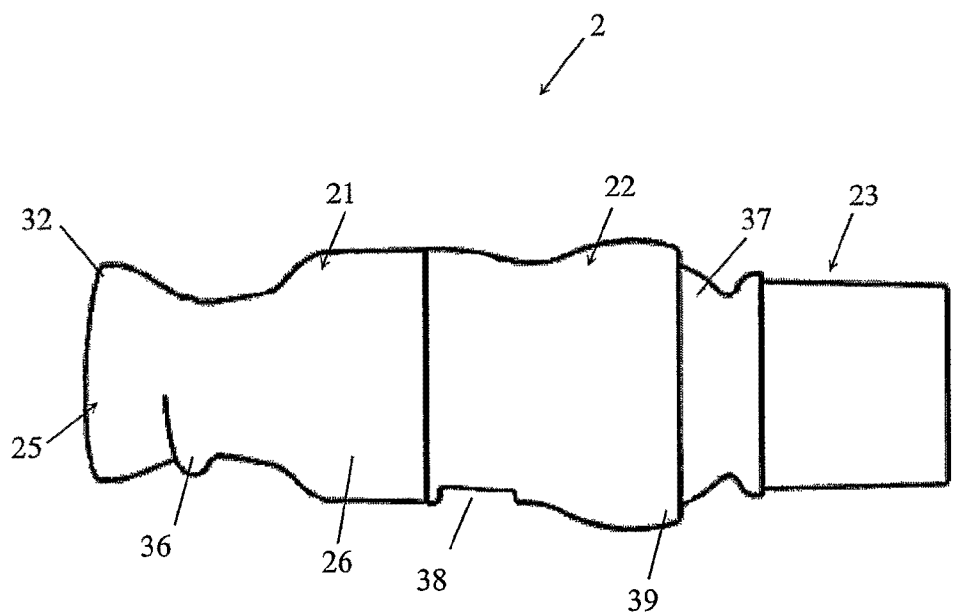
FIG. 3 is a side view of the nasal cannula of FIG. 2.
Figure 4:
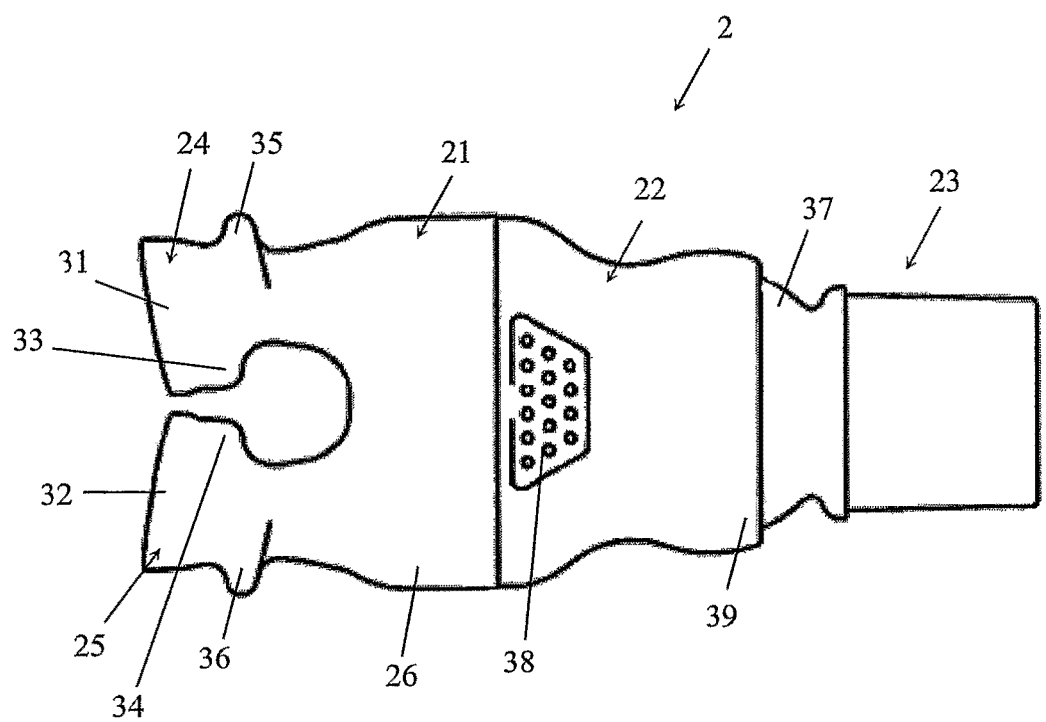
FIG. 4 is a plan view of the nasal cannula of FIG. 2.
Figure 5:
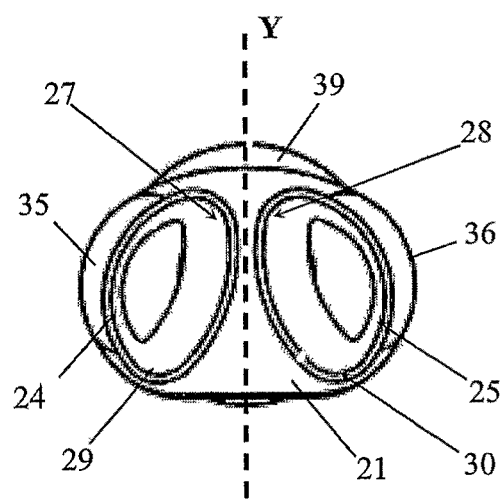
FIG. 5 is a prong end view of the nasal cannula of FIG. 2
Figure 6:
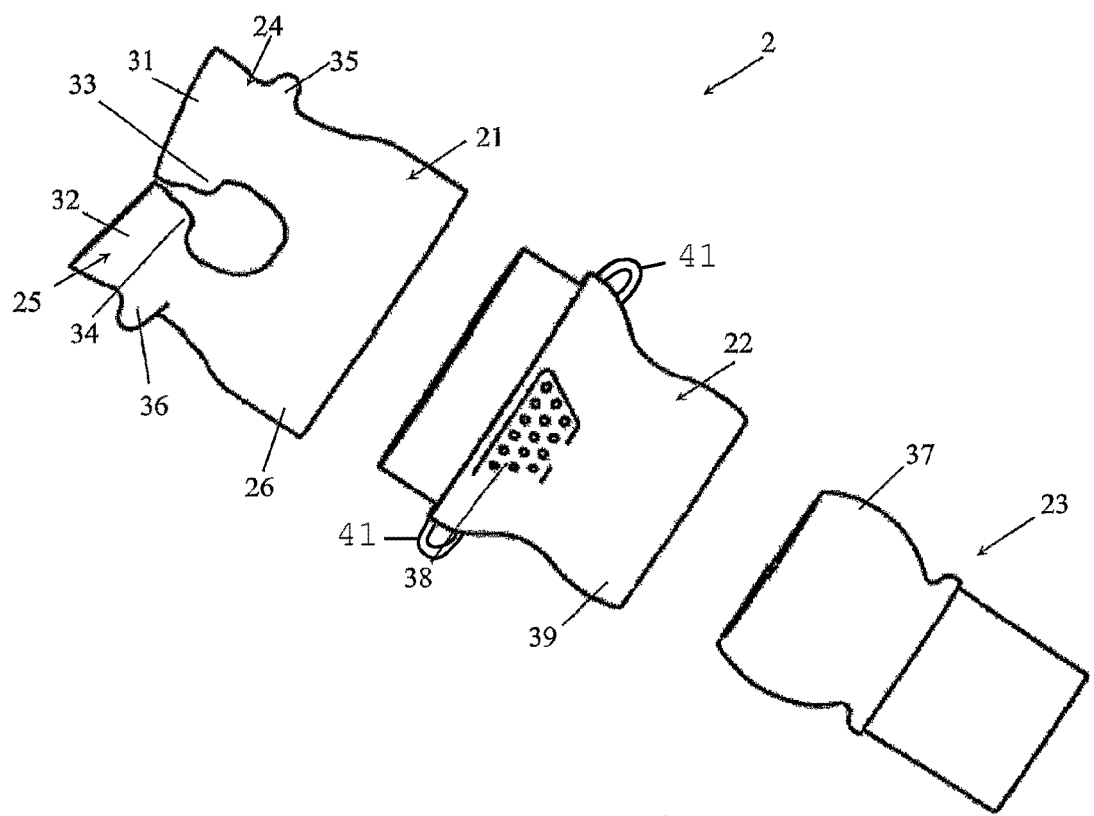
FIG. 6 is an exploded view of the nasal cannula of FIG. 2.

A first embodiment of a nasal cannula of the present invention is shown in detail in FIGS. 2 to 6. Referring to FIGS. 2 and 6, the nasal cannula 2 comprises three main components; the prong part 21, body part 22 and ball connector 23.

The prong part 21 has two nasal prongs 24, 25, each of which are substantially shaped to follow the contours of the human nares and in use are placed inside a user's nares. The prongs 24, 25 extend out from a hollow tubular body 26 that in use fits to the body part 22. Each of the prongs 24, 25 are integrally moulded with the tubular body 26 in a flexible plastics material or rubber, such as silicone, other thermoset elastomers or thermoplastic elastomers such as Kraton™. The prongs 24, 25 are substantially oval tubular members that allow for a passage of gases. In particular, as shown in FIG. 5, the prongs are oval in shape and angled in the same manner as a human's nares. The prongs 24, 25 are angled toward one another (or toward the vertical axis Y) at the top 27, 28 of the prongs and away from one another at the bottom 29, 30 of the prongs. Furthermore, the ends 31, 32 of the prongs flare outwardly and preferably are formed such that the ends of the prongs are thinner in cross-section than the rest of the prongs. The flared thinner section ends 31, 32 of the prongs assist with the sealing of the prongs 24, 25 in use within the user's nares. When in use and with gases flowing through the prongs the force of the gas pressure will force the prong ends 31,32 to flare outwardly and seal against the inside of the user's nares.

The prongs 24, 25 each include a step 33, 34 formed along their lengths. Each of the steps 33, 34 are formed on the prongs 24, 25 in an opposing manner such that in use, when the prongs are within a user's nares the steps 33, 34 abut the user's nasal septum and form a ledge that prevents dislodgement of the prongs. The prongs 24, 25 also have protrusions 35, 36 formed on their outer edges that abut the sides of the user's nares (opposite to the nasal septum). The protrusions 35, 36 assist in preventing the dislodgement of the prongs, especially if the user moves his or her head. The protrusions 35, 36 also maintain the prongs within the user's nares in a correct orientation such that in use gases flow through the prongs and directly up the user's nasal passages.

The body part 22 is a tubular passageway in which the prong part 21 is connected at one end and a ball joint 37 at the other end. The ball joint 37 extends from the connector 23 and slots into a complementary shaped (partial sphere) socket end 39. The body part 22 also has a number of apertures 38 formed in it, which act as a bias flow outlet vent. Therefore, any gases exhaled by the user through their nose will exit through the apertures 38.

The connector 23 is preferably connected to the inspiratory conduit 3 (see FIG. 1) that supplies gases flow to the cannula 2. The inspiratory conduit 3 may be moulded directly to the connector 23 or other connection mechanisms may be used, such as a friction fit formed between the connector and conduit.

Although a ball and socket joint, as described above, between the body part 22 and connector 23 is preferred other connections may be utilised, such as a flexible piece of silicone, or other appropriate connection. The connection between the cannula body and connector must be able to be flexed or rotated to allow for the inspiratory conduit 3 to be moved without causing the dislodgement of the nasal cannula 2 from the user's nares.

In the preferred form of the nasal cannula 2 of the present invention the body part 22 and connector 23 are preferably made from a hard or rigid plastics material, such as polypropylene, polycarbonate or acetyl. In other forms the body part 22 and connector 23 may be of different plastics materials to allow for increased slidability between these parts.

The prong part 21 may be supplied in various different sizes such that different sized user's may remove an existing prong part and simply attach a different sized flexible plastics prong part over the body part 22.

To provide additional comfort for the user or ensure the nasal cannula of the present invention do not fall from a user's nares, the nasal cannula may be used in combination with a headgear strap, which in one embodiment is a small flexible tube. For example, FIG. 1 shows a headgear strap 40 extending from the nasal cannula 2. The ends of the headgear strap that attach to the cannula may attach to extensions (or loops) 41 on the body part 22 of the cannula shown in FIG. 2, or may attach about other appropriate areas of the cannula, for example, about the connector 23.

The abovementioned embodiment of the nasal cannula 2 of the present invention is preferably a wide bore pronged cannula used for high flow conditions.

Figure 7:
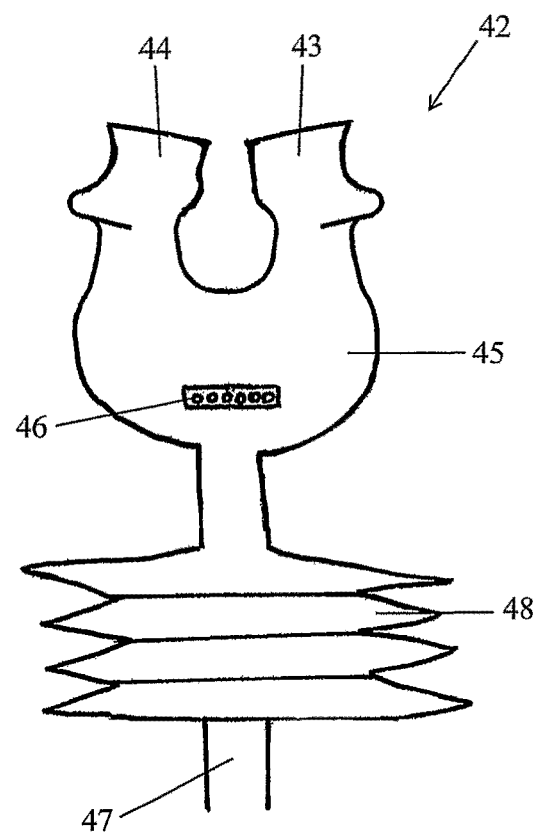
FIG. 7 is a side view of a second embodiment of a nasal cannula of the present invention.

A second embodiment of the present invention is shown in FIG. 7. In this embodiment of the nasal cannula 42 the prongs 43, 44 are preferably small bore prongs for use with lower flow conditions. The prongs 43, 44 are similarly shaped to the prongs 24, 25 detailed above, but may not seal in the same manner as the abovementioned prongs due to the smaller size of the prongs. In fact these prongs may not seal at all in use within the user's nares.

Furthermore, in this second embodiment the nasal cannula 42 is smaller and weighs less as it is only comprised of a prong body 45 and prongs 43, 44, where the body 45 is connected to a small tube that is formed with corrugations or bellows 48 that connect to an inspiratory tube or conduit 47 (similar to the inspiratory conduit 3 described above) that receives a supply of gases.

The corrugations of bellows 48 will bend or move when a weight or force is placed on the cannula, thereby preventing dislodgement of the cannula 42 from a user's face in use. In particular, the corrugations or bellows 48 prevent transferral of the torque onto the cannula 42 when a user moves his or her head.

The body 45 of the cannula 42 is provided with a number of apertures 46 that allows for gases exhaled by the users to be expelled into the ambient air.

The prong body and prongs of this embodiment of the cannula of the present invention are preferably formed a flexible plastics material or rubber, such as silicone, other thermoset elastomers or thermoplastic elastomers such as Kraton™.

Figure 8:
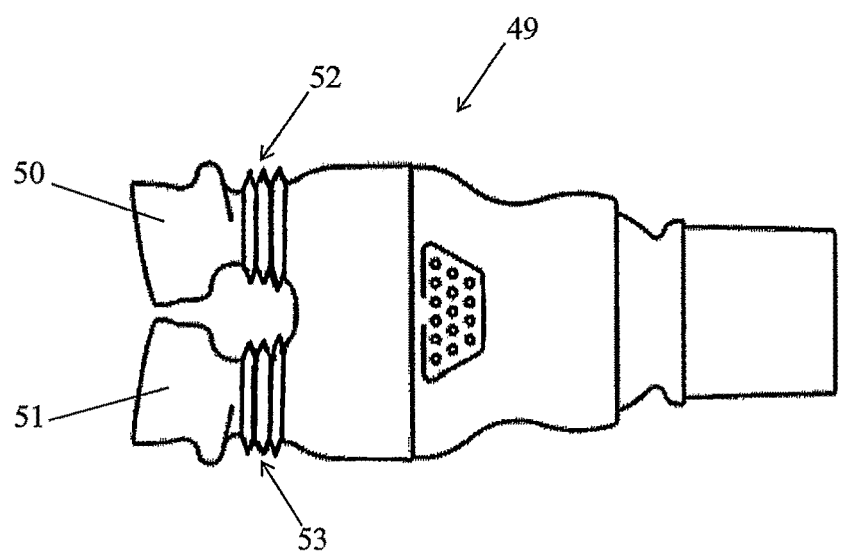
FIG. 8 is a side view of a third embodiment of a nasal cannula of the present invention.
Figure 9:
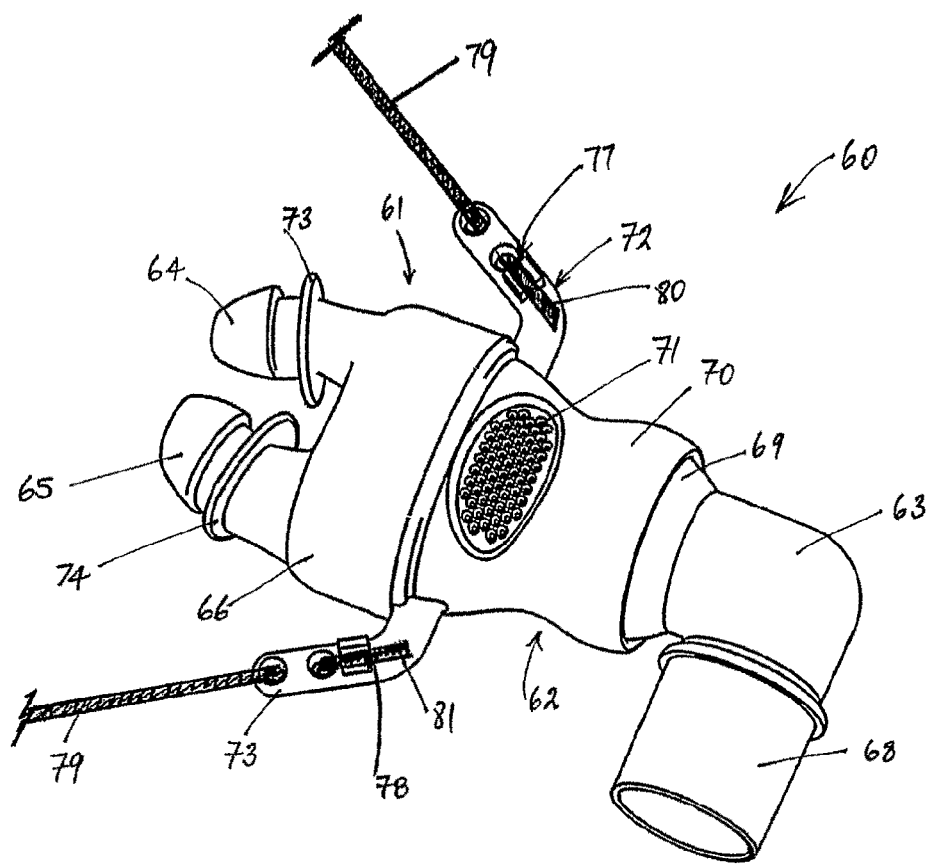
FIG. 9 is a perspective view of a fourth embodiment of a nasal cannula of the present invention.

A third embodiment of the nasal cannula of the present invention is shown in FIG. 8 where the cannula may be provided with corrugated or baffled sections on the prongs. The nasal cannula 49 of this embodiment is similar to that of FIG. 2 but the prongs 50, 51 have a series of corrugations 52, 53 formed in them. The corrugations 52, 53 allow for movement of each of the prongs 50, 51 for a better user fit, and allow for movement of the cannula 49 without causing dislodgement of the prongs from the user's nares.

Angled Prong Nasal Cannula

A fourth embodiment of the nasal cannula of the present invention is shown in FIGS. 9 to 13. The nasal cannula 60 has a similar construction to the nasal cannula of FIG. 2 and comprises three main components; a prong part 61, body part 62 and ball jointed connector 63.

The prong part 61 preferably has two nasal prongs 64, 65, each of which are substantially shaped to follow the contours of the human nares and in use are placed inside a user's nares. In some forms a cannula with only one prong may be provided. The prongs 64, 65 extend out from a hollow tubular body 66 that in use fits to the body part 62, preferably about an extension 67 (as shown in the exploded view of the nasal cannula of FIG. 11). Each of the prongs 64, 65 are integrally moulded with the tubular body 66 in a flexible plastics material or rubber, such as silicone, other thermoset elastomers or thermoplastic elastomers, such as Kraton™. The prongs 64, 65 are substantially oval tubular members that allow for a passage of gases.

Figure 12:
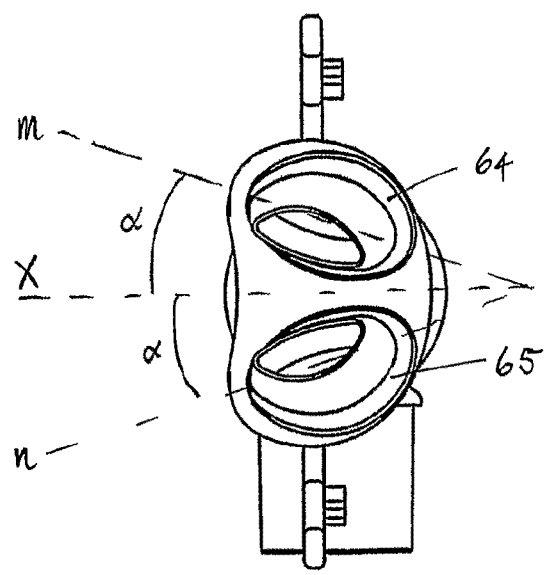
FIG. 12 is a front view of the prongs of the nasal cannula of FIG. 9.
Figure 13:
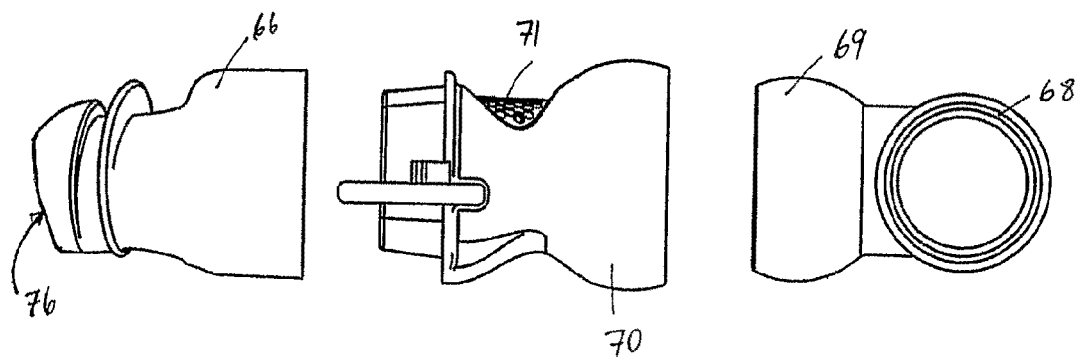
FIG. 13 is an exploded side view of the nasal cannula of FIG. 9.

In particular, as shown in FIG. 12, the prongs are oval in shape (to reflect the shape of human nares) and angled in the same manner as a human's nares. The prongs 64, 65 are angled toward one another (or toward the horizontal axis X) such that angles .alpha. are formed between the midlines m, n through each respective prong 64, 65. The angled profile of the prongs 64, 65 means that they are more ergonomically correct with a human's nares and may assist in directing the gases flow from the prongs to the user's nasal cavities. The prongs 64, 65 are constructed such that their cross-sectional width narrows closer to the tip of each prong.

Figure 10:
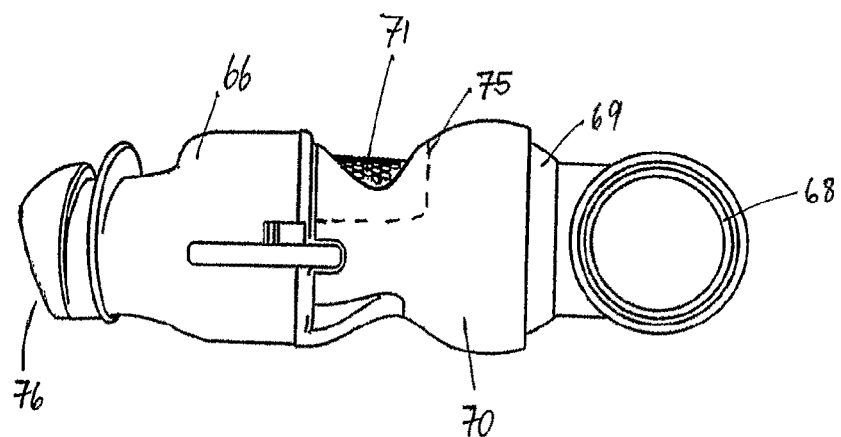
FIG. 10 is a side view of the nasal cannula of FIG. 9.
Figure 11:
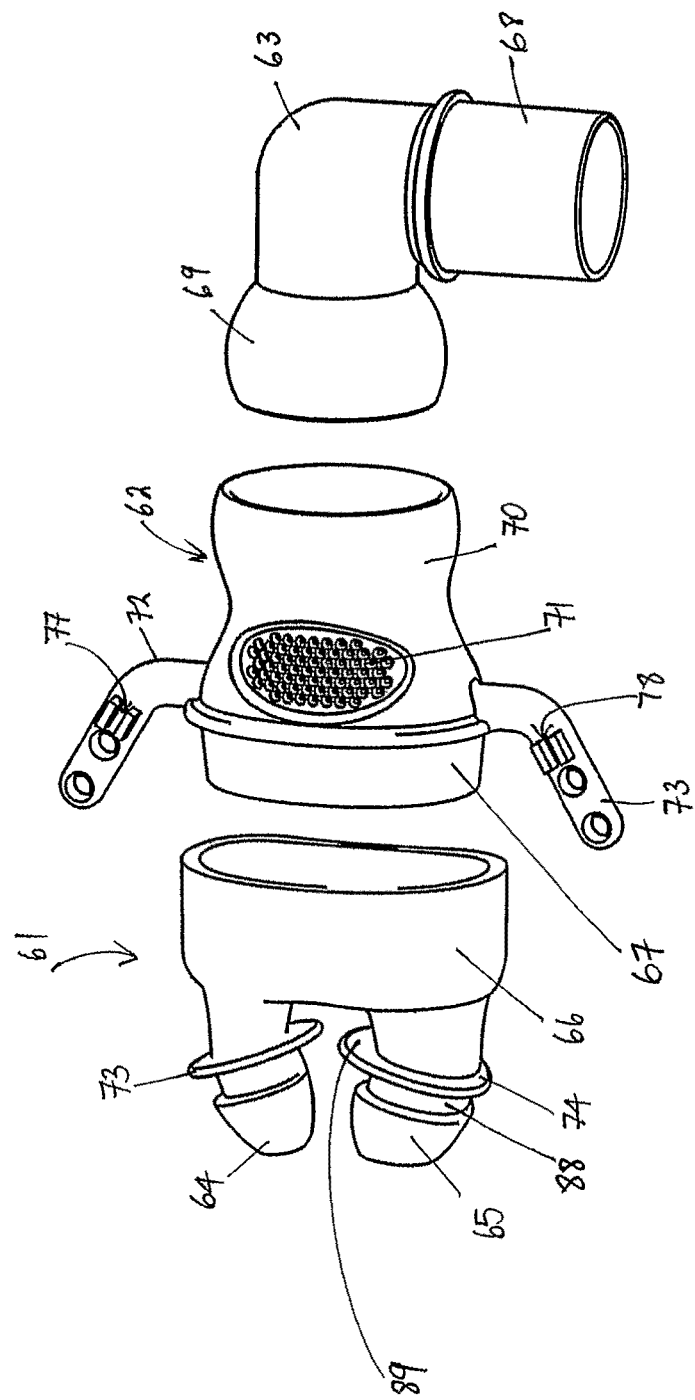
FIG. 11 is an exploded perspective view of the nasal cannula of FIG. 9.

In the preferred form the prongs 64, 65 have an angled and profiled end 76 (see FIG. 10). The angled ends 76 assist in directing gases flow to the user's nasal passages.

Each of the prongs 64, 65 has a flange 73, 74 disposed about its circumference. The flanges 73, 74 are at a position on the prongs 64, 65 such that the each of the flanges rests against the outside of each of the patient's nares. The flanges 73, 74 do not extend inside the nares, but rest at the entranceway of the user's nares, and preferably seal the nares. In some users the flanges 73, 74 may extend within the user's nares and provide sealing of the nares. The flanges 73, 74 are preferably thin flexible extensions that extend substantially completely around the circumference of the prongs 64, 65. The flanges 73, 74 are preferably substantially elliptical in shape with one side (for example, side 89, which in use will abut the nasal septum of a user) of the flange extending out from each prong further than the other side of each prong. There is a recessed area 88 on each of the prongs between the flange and the shaped ends of the prongs in which preferably in use the ends of a user's nares rest.

The body part 62 is a tubular passageway in which the prong part 61 is connected at one end and a ball joint 69 at the other end. The ball joint 69 extends from the connector 63 and slots into a complementary shaped (partial sphere) socket end 70 on the body part 62. The body part 62 may also have a plurality of apertures 71 formed in it, which acts as a bias flow outlet vent. Therefore, any gases exhaled by the user through their nose will exit through the apertures 71.

A shield 75 (illustrated by the dashed line in FIG. 10) may extend over the bias vent 71 inside the body part 70 to prevent gases from the blower (gases supply 15) from interacting with the bias vent 71 and vent holes, causing noise in use.

Figure 16:
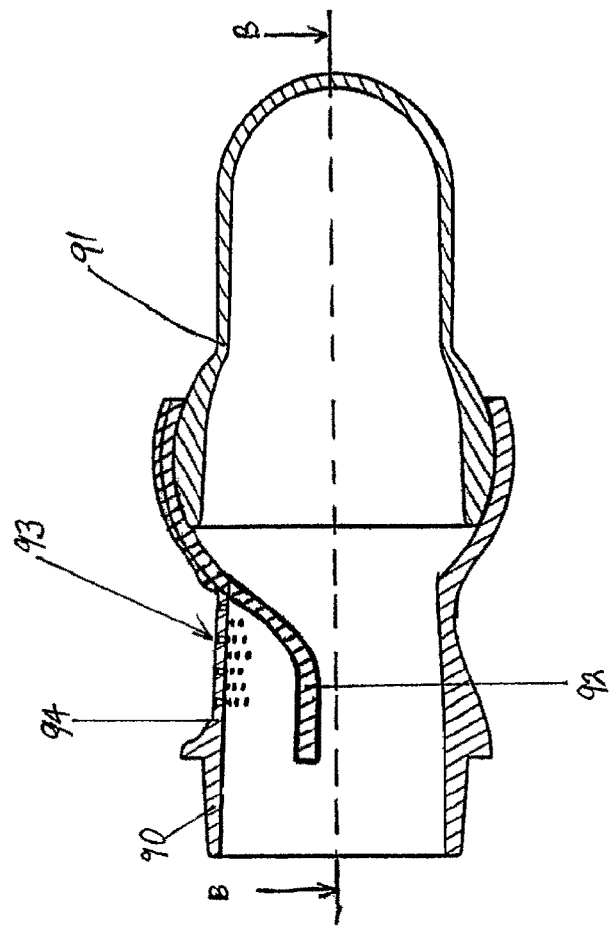
FIG. 16 is a side cross-sectional view of a sixth embodiment of the nasal cannula of the present invention including a shield that protects an outlet vent from inlet gases.
Figure 17:
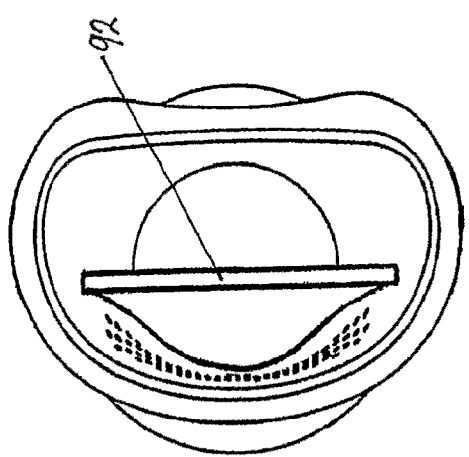
FIG. 17 is a cross-section through BB of the nasal cannula of FIG. 16.

In a sixth embodiment as shown in FIGS. 16 and 17 a nasal cannula without a prong part is shown, but that includes a shield similar to that described above. In this embodiment a body part 90 and a ball jointed connector 91 fit together as described above. The body part 90 includes an expiratory vent shield 92 that extends down from the top wall 94 of the body part 90 and shields the outlet vent 93.

Referring back to FIGS. 10 to 13, preferably the ball joint connector 63 is angled and extends into a swiveable connector 68. The swivel connector 68 is capable in use of being connected to the inspiratory conduit 3 (see FIG. 1) that supplies gases flow to the cannula 60. The inspiratory conduit 3 may be moulded directly to the connector 68 or other connection mechanisms may be used, such as a friction fit formed between the connector 68 and the conduit 3.

In other forms of the present invention the ball joint connector 63 or the ball joint 69 may have formed in it a plurality of channels. One example of this is the embodiment of FIGS. 14 and 15. Such channels allow there to be a leak when gases flow through the connector to the cannula and prongs. The channels are therefore capable of acting as a bias flow and a separate bias flow out outlet (such as that outlet 71 described above) may not be required.

Figure 14:
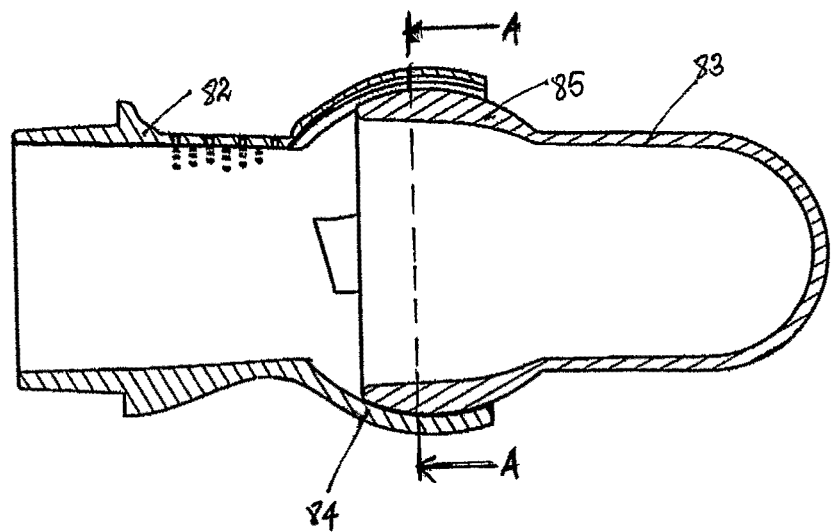
FIG. 14 is a side cross-sectional view of a fifth embodiment of the nasal cannula of the present invention where the connection between a body part and connector of the cannula includes a plurality of channels.
Figure 15:
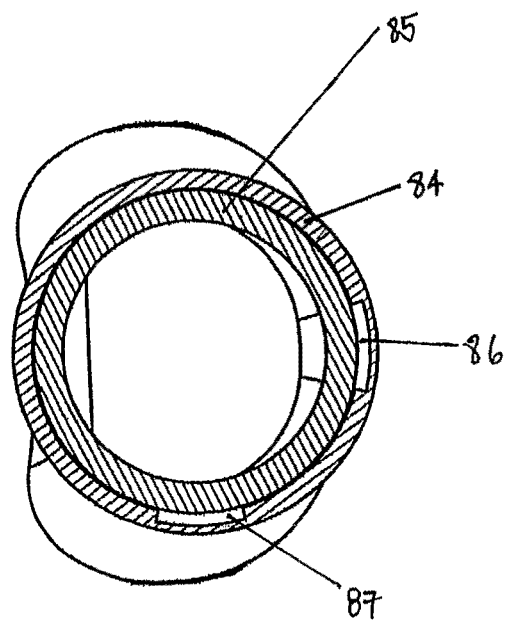
FIG. 15 is a cross-section through AA of the nasal cannula of FIG. 14.

In FIGS. 14 and 15 only a body part 82 and ball jointed connector 83 are shown. The body part 82 and ball jointed connector 83 join in a manner as described above, where the substantially half sphere shaped end 84 of the body part 82 receives the substantially half sphere shaped end 85 of the connector 83. The ends 84, 85 enable a rotation between the body part 82 and connector 83. In this embodiment two channels 86, 87 are formed in the connector end 85. Two channels are shown in this embodiment but there may be only one or any number of channels. Similarly, channels may be formed in the body part end 84.

It is preferred that there is a ball and socket joint, as described above, between the body part 62 and connector 63, although other connections may be utilised, such as a flexible piece of silicone, or other appropriate connection. The connection between the cannula body and connector must be able to be flexed or rotated to allow for the inspiratory conduit 3 to be moved without causing the dislodgement of the nasal cannula 60 from the user's nares.

In the preferred form of the nasal cannula 60 of the present invention the body part 62, connector 63, ball joint 69 and swivel connector 68 are preferably made from a hard or rigid plastics material, such as polypropylene, polycarbonate or acetyl. In other forms these may be of different plastics materials to allow for increased slidability between these parts.

The prong part 61 may be supplied in various different sizes such that different sized user's may remove an existing prong part and simply attach a different sized flexible plastics prong part over the body part 62.

To provide additional comfort for the user or ensure the nasal cannula of the present invention does not fall from a user's nares, the nasal cannula 60 is preferably used in combination with a headgear strap. The strap may be similar to that shown in FIG. 1 with relation to the first form of the nasal cannula 2. In this fourth form of the nasal cannula 60 the body part 62 has headgear extensions 72, 73 that extend out from the body part 70. The extensions 72, 73 each have a channel 77, 78 formed in them that is capable of receiving an end 80, 81 of the headgear strap 79. The strap ends 80, 81 in use are threaded through apertures (preferably two) and extend into and are held in the channels 77, 78. In this form the headgear strap 79 is made from a small diameter silicon, rubber or similar type material. Therefore, when the strap ends 80, 81 are threaded through the apertures friction is created that maintains the straps within the apertures and prevents the straps from slipping from the cannula.

In other forms the ends of the headgear strap that attach to the cannula may attach to extensions (or loops) 41 on the body part 22 of the cannula shown in FIG. 6, or may attach about other appropriate areas of the cannula, for example, about the connector 23.

What is claimed is:

1. A mask assembly for delivering positive airway pressure to a user, the mask comprising:
    a rigid mask body comprising a central portion, an outer surface having at least a curved portion and a mask body periphery, the mask body periphery comprising a left peripheral side and a right peripheral side;
    a prong part comprising a hollow body removably sealed to the rigid mask body defining an enclosed space, a prong part periphery extending along a periphery of the hollow body, and first and second nasal prongs extending from the hollow body, the periphery of the prong part removably sealed to the mask body periphery in use, the prong part being formed as a single piece and being more flexible than the rigid mask body;
    an inspiratory conduit connected to the rigid mask body configured to deliver pressurized gases into the enclosed space defined by the rigid mask body and the prong part for inhalation by a user in use;

a headgear arrangement configured to maintain the prong part in a position with the first and second prongs against a user's nares in use, the headgear arrangement comprising first and second headgear extensions and a headgear strap;

the first headgear extension having a distal end connected to the left peripheral side of the rigid mask body on a distal side of the prong part at a location spaced from a user in use, and a proximal end disposed proximally toward a left side of a user's face in use, the first headgear extension comprising a first portion and a second portion, the first portion of the first headgear extension comprising the distal end of the first headgear extension and extending at least along a first lateral direction extending laterally away from the left peripheral side of the rigid mask body and beyond an outer periphery of the prong part, the second portion of the first headgear extension extending from the first portion, along a second direction extending more proximally toward the user than the first direction in use;

the second headgear extension having a distal end connected to the right peripheral side of the rigid mask body on the distal side of the prong part at a location spaced from a user in use, and a proximal end disposed proximally toward a right side of a user's face in use, the second headgear extension comprising a first portion and a second portion, the first portion of the second headgear extension comprising the distal end of the second headgear extension and extending at least along a third lateral direction extending laterally away from the rigid mask body and beyond the outer periphery of the prong part, the second portion of the second headgear extension extending from the first portion, along a fourth direction extending more proximally toward the user than the third direction in use;

the headgear strap comprising a flexible tube having first and second ends, the first end connected to the first headgear extension at a first location between the distal end and the proximal ends of the first headgear extension and a second end connected to the second headgear extension at a second location disposed between the proximal and distal ends of the second headgear extension; and at least a first bias flow vent disposed on the curved portion of the outer surface of the rigid mask body, the first bias flow vent being configured to vent a gas from the enclosed space between the rigid mask body and the prong part, to an outside of the rigid mask body during use.

2. The mask assembly of claim 1, wherein the first bias flow vent comprises a flow vent outer surface, the flow vent outer surface being recessed inwardly from the curved portion of the outer surface of the rigid mask body.

3. The mask assembly of claim 1, additionally comprising a conduit connection disposed on the rigid mask body and connecting the inspiratory conduit to the rigid mask body, the first bias flow vent comprising a plurality of apertures arranged symmetrically on left and right sides of the conduit connection.

4. The mask assembly of claim 1, wherein the rigid mask body is configured to direct gases entering the rigid mask body from the conduit away from the bias flow vent.

5. The mask assembly of claim 4, wherein the rigid mask body is configured to direct gases entering the rigid mask body from the prong part toward the bias flow vent.

6. A mask assembly for delivering positive airway pressure to a user, the mask comprising:

a rigid mask body comprising a central portion, an outer surface having at least a curved portion;

an inspiratory conduit connected to the rigid mask body;

a prong part comprising a hollow body and first and second nasal prongs extending from the hollow body, the hollow body removably connected to the mask body;

a first headgear extension having a distal end connected to the rigid mask body on a distal side of the prong part at a location spaced from a user in use, and a proximal end disposed proximally toward a user in use, the first headgear extension comprising a first portion and a second portion, the first portion of the first headgear extension comprising the distal end of the first headgear extension and extending at least along a first lateral direction extending laterally away from the rigid mask body and beyond an outer periphery of the prong part, the second portion of the first headgear extension extending from the first portion, along a second direction extending more proximally toward the user than the first direction in use;

a second headgear extension having a distal end connected to the rigid mask body on the distal side of the prong part at a location spaced from a user in use, and a proximal end disposed proximally toward a user in use, the second headgear extension comprising a first portion and a second portion, the first portion of the second headgear extension comprising the distal end of the second headgear extension and extending at least along a third lateral direction extending laterally away from the rigid mask body and beyond the outer periphery of the prong part, the second portion of the second headgear extension along a fourth direction more proximally toward the user than the third direction in use; and a headgear strap connected to the first headgear extension at a first location between the distal end and the proximal ends of the first headgear extension and connected to the second headgear extension at a second location disposed between the proximal and distal ends of the second headgear extension.

7. The mask assembly of claim 6, wherein the first portion of the first headgear extension is shorter than the second portion of the first headgear extension and the first portion of the second headgear extension is shorter than the second portion of the second headgear extension.

8. The mask assembly of claim 6, wherein the headgear strap comprises a flexible tube and is connected to the second portion of the first headgear extension and the second portion of the second headgear extension.

9. The mask assembly of claim 6, wherein the first portion of the first headgear extension and the first portion of the second headgear extension extend laterally outward distally of a sealing location between the prong part and the mask body and the second portion of the first headgear extension and the second portion of the second headgear extension terminate proximally of the sealing location between the prong part and the mask body.

10. The mask assembly of claim 6, wherein the headstrap comprises first and second ends, the first end extending along first and second opposite sides of the second portion of the first headgear extension at the connection to the first headgear extension, the second end extending along first and second opposite sides of the second portion of the second headgear extension at the connection to the second headgear extension.

11. The mask assembly of claim 6, wherein the second portion of the first headgear extension and the second portion of the second headgear extension terminate proximally of a mating region between the hollow body of the prong portion and the rigid mask body.

12. The mask assembly of claim 6, wherein the hollow body of the prong portion and the rigid mask body overlap each other in a mating region.

13. The mask assembly of claim 12, wherein the hollow body, the first prong and the second prong are integrally formed in a monolithic component.

14. The mask assembly of claim 12, wherein the first prong and the second prong are angled toward each other in the proximal direction.

15. The mask assembly of claim 6, wherein the rigid mask body comprises a recessed curved portion of the curved outer which is recessed inwardly into the rigid mask body relative to a surrounding portion of the curved outer surface, the recessed curved portion comprising a plurality of apertures defining a bias flow outlet vent.

16. The mask assembly of claim 6, wherein the rigid mask body is configured to direct gases entering the rigid mask body from the conduit away from the bias flow vent, and to direct gases entering the rigid mask body from the prong part toward the bias flow vent.

17. A mask assembly for delivering positive airway pressure to a user, the mask comprising:
 a rigid mask body;
 an inspiratory conduit connected to the rigid mask body;
 a prong part comprising a hollow body and first and second nasal prongs extending from the hollow body, the hollow body removably connected to the mask body;
 a first headgear extension having a distal end connected to the rigid mask body on a distal side of the prong part at a location spaced from a user in use, and a proximal end disposed proximally toward a user in use, the first headgear extension extending from the rigid mask body, at least along a first lateral direction extending laterally away from the rigid mask body and beyond an outer periphery of the prong part and along a second direction extending more proximally toward the user than the first direction in use; and
 a second headgear extension having a distal end connected to the rigid mask body on the distal side of the prong part at a location spaced from a user in use, and a proximal end disposed proximally toward a user in use, the second headgear extension extending from the rigid mask body at least along a third lateral direction extending laterally away from the rigid mask body and beyond the outer periphery of the prong part and along a fourth direction more proximally toward the user than the third direction in use.

18. The mask assembly of claim 17 additionally comprising a headgear strap connected to the first headgear extension at a first location between the distal end and the proximal ends of the first headgear extension and connected to the second headgear extension at a second location disposed between the proximal and distal ends of the second headgear extension.

19. The mask assembly of claim 18, wherein the headgear strap comprises a flexible tube engaged with the first and second headgear extensions.

\* \* \* \* \*